(12) United States Patent
Gan

(10) Patent No.: US 8,040,498 B2
(45) Date of Patent: Oct. 18, 2011

(54) METHOD AND SYSTEM FOR IDENTIFICATION OF CHANGES IN FLUIDS

(75) Inventor: Livne Gan, Medereshet Ben Gurion (IL)

(73) Assignee: Virtue Sense Ltd., Rosh HaAyin (IL)

( * ) Notice: Subject to any disclaimer, the term of this patent is extended or adjusted under 35 U.S.C. 154(b) by 788 days.

(21) Appl. No.: 10/580,475

(22) PCT Filed: Nov. 24, 2003

(86) PCT No.: PCT/IL03/00987
§ 371 (c)(1),
(2), (4) Date: Sep. 2, 2008

(87) PCT Pub. No.: WO2005/050179
PCT Pub. Date: Jun. 2, 2005

(65) Prior Publication Data
US 2008/0309937 A1    Dec. 18, 2008

(51) Int. Cl.
*G01N 21/41* (2006.01)
(52) U.S. Cl. .......................... 356/128; 356/133
(58) Field of Classification Search .......... 356/128–135; 250/237 R, 237 G; 340/618–619
See application file for complete search history.

(56) References Cited

U.S. PATENT DOCUMENTS

| | | |
|---|---|---|
| 4,569,590 A | 2/1986 | Karny et al. |
| 4,722,605 A | 2/1988 | Livnat et al. |

FOREIGN PATENT DOCUMENTS

| | | |
|---|---|---|
| EP | 1 324 015 | 7/2003 |
| GB | 1 508 783 | 4/1978 |

OTHER PUBLICATIONS

Anonymous, "Automated Detector for Liquid Chromatography. Sep. 1976.", IBM Technical Disclosure Bulletin, vol. 19, No. 4, Sep. 1, 1976, p. 1262.

(Continued)

*Primary Examiner* — Tri T Ton
(74) *Attorney, Agent, or Firm* — Pearl Cohen Zedek Latzer, LLP

(57) ABSTRACT

Method and system for identification of a changed state of a fluid with respect to a reference state of the same fluid, the fluid having an optical parameter changing with the change of the state of the fluid. The method comprises: a) providing an optical arrangement including a transparent enclosure with a portion of the fluid, and an object observable through the optical arrangement, the arrangement being designed such that an image of the object in the changed state of the fluid is optically distinctive from an image of the object in the reference state of the fluid due to change of the optical parameter, at least one of the images being predetermined; b) illuminating the object with diffuse light; c) observing a current image of the object though the optical arrangement along an optical axis; and d) comparing the current image to the predetermined image to identify the changed state of the fluid. The comparison and the identification may be performed by eye or by a sensor with a logical circuit.

2 Claims, 3 Drawing Sheets

OTHER PUBLICATIONS

Anonymous, "Nonrefractive Method of Determining Low Concentration Impurity Levels in Liquids, Aug. 1975", IBM Technical Disclosure Bulletin, vol. 19, No. 3, Aug. 1, 1975, pp. 696-697.

Mishra D. et al., "Development of a coherent gradient-sensing tomographic interferometer for three-dimensional refractive index-based measurements", Optics Communications, North-Holland Publishing Co., Amsterdam, NL, vol. 212, No. 1-3, Oct. 15, 2002, pp. 17-27.

Song J S et al., "Moiré patterns of two different elongated circular gratings for the fine visual measurement of linear displacements", Optics Communications, North-Holland Publishing Co., Amsterdam, NL, vol. 154, No. 1-3, Aug. 15, 1998, pp. 100-108.

International Search Report for PCT/IL03/00987, mailed on Sep. 7, 2004.

International Search Report for International Application No. PCT/IL03/00987 mailed Sep. 7, 2004.

METHOD AND SYSTEM FOR IDENTIFICATION OF CHANGES IN FLUIDS

FIELD OF THE INVENTION

This invention relates to the examination of fluids based on their optical properties.

BACKGROUND OF TEE INVENTION

There exist systems for measuring optical properties of fluids. U.S. Pat. No. 4,569,590 to Karney describes a system for determining unknown index of refraction of a sample fluid with reference to the refraction index of a known reference fluid. The system comprises a collimated light source, a light pervious cell formed as a biconvex lens fillable with a fluid, a pair of gratings and a screen. Collimated light is directed through the cell filled first with the reference fluid and then with the sample fluid, onto the gratings, and reference and sample patterns are obtained thereby on the screen. The sample pattern will be different from the reference one if the optical power of the biconvex lens changes due to the change of the liquid in the cell. The difference between the reference pattern and the sample pattern is then measured and used for calculating the refraction index of the sample fluid.

EP 1324015 describes similar techniques for measuring optical parameters of a phase object based on recording a moiré pattern viewed through the phase object. The moiré pattern is formed by illuminating two gratings by diffuse light, and projecting their images on a screen through the phase object. The optical parameters of the phase object are calculated from the moiré pattern.

Such methods require relatively complex optical systems, recording and measurement of images and sophisticated calculations in order to determine accurately a change in the optical parameter of the liquid.

SUMMARY OF THE INVENTION

The present invention makes use of the idea that small changes in optical properties of some fluids may be indicative of expected or unwanted changes in their composition, temperature and other non-optical properties. Thus, changes both of optical and non-optical properties may be monitored and detected by means of optical observations. In the following, terms like "optical" or "light" will refer to visible, ultraviolet and infrared light; words like "detect", "observe", "identify", "view" will refer both to human eye and to sensors. The term "change" will pertain, inter alia, to change of phase such as freezing, evaporation, etc; to change of structure such as setting, coagulation, etc; to evacuation, loss of vacuum, pressurization or depressurization.

In accordance with the present invention, there is provided a method for identification of a changed state of a fluid with respect to a reference state of the same fluid, the fluid having an optical parameter changing with the change of the state of the fluid, the method comprising:

a) providing an optical arrangement including a transparent enclosure with a portion of the fluid, and an object observable through the optical arrangement, the arrangement being designed such that an image of the object in the changed state of the fluid (changed image) is optically distinctive from an image of the object in the reference state of the fluid (reference image) due to change of the optical parameter, at least one of the images being predetermined (known);

b) illuminating the object with diffuse light;

c) observing a current image of the object through the optical arrangement along an optical axis; and d) comparing the current image to the predetermined image to identify the changed state of the fluid.

The comparison and the identification in step (d) may be performed by eye or by a sensor with a logical circuit.

The diffuse light may be visible or in the UV or IR spectrum. In the latter case, the optical arrangement may include converter to visible light.

The predetermined image may be known to a human observer from previous experience or verbal description, or may be depicted or described on or close to the optical arrangement. Alternatively, the predetermined image may be recorded in the optical arrangement and be made visible therein simultaneously with the current image, e.g. superimposed thereon for easier comparison.

Such optical parameter may be any parameter that would provide detectable difference in the images of the observed object as, for example, the refraction index of the fluid in reference and changed states of the fluid, but may be also the angle of polarization, or the index of absorption, the absorption spectrum, the reflection spectrum, etc. Changes in the structure of the fluid can also be detected, such as due to turbidity, setting, phase change, etc.

According to a second aspect of the present invention, there is provided an optical arrangement for identification of a changed state of a fluid with respect to a reference state of the fluid, the fluid having an optical parameter changing with the change of the state of the fluid, such as, for example, the refraction index of the fluid. The optical arrangement comprises:

a) a transparent enclosure adapted to be filled with at least a portion of the fluid;

b) an object observable through the enclosure, c) an optical system having an optical axis and enabling the observation of the object when illuminated by diffuse light, via the enclosure filled with said fluid.

The optical arrangement is designed such that an image of the object observed in the changed state of the fluid is optically distinctive from an image of the object observed in the reference state of the fluid, due to a change of the optical parameter. At least one of the reference image and the changed image is predetermined, so that the identification can be done by comparing a current image of the object to the predetermined image.

The optical arrangement may comprise a source of diffuse light. The light may be in the UV or IR spectrum, and the arrangement may comprise also a converter to visible light. Alternatively, the ambient light may be used.

The optical system may be adapted to form the current image on the retina of the eye. Alternatively, the optical system may be adapted to form the current image on a screen. The image may also be viewed via a video camera. In the latter two cases, the optical system comprises a small aperture in front of the eye, the screen or in the video camera.

The optical arrangement may comprise a sensor with logical circuit adapted to perform the identification instead of the human eye.

Preferably, the transparent enclosure, when filled with the fluid in one of the states (the changed state or the reference state), constitutes a lens or a prism with zero power, while when filled with the fluid in the other state, it constitutes a lens or prism with non-zero power. However, working arrangement may be obtained also when the transparent enclosure constitutes a lens or a prism with non-zero but different power in both states of the fluid. The transparent enclosure is preferably located between the object and the eye/screen/video camera.

The observable object may comprise gratings disposed in parallel planes spaced along the optical axis, e.g. a pair of Ronchi rulings such as disclosed in EP 1324015.

The optical arrangement may comprise a record of the predetermined image and means for the demonstration of the record to a human observer simultaneously with the current image, for example a printed pattern in the field of view. The optical arrangement may comprise means for superimposing the current image on the record of the predetermined image.

In one specific example of the optical arrangement of the present invention, the optical parameter used for the identification of the change of state is the refraction index of the fluid. A portion of the fluid fills an enclosure defined between two concavo-convex lenses. On one side of the enclosure there are disposed two Ronchi rulings in parallel planes spaced along the optical axis. On the other side of the enclosure and spaced therefrom along the optical axis is a small viewer, i.e. the eye of the observer, or the screen or video camera with an aperture, or a sensor. From all diffused light beams illuminating the two Ronchi rulings, parallel beams are focused at a location spaced from the enclosure where the eye's pupil or the aperture are disposed. These beams form images of the rulings on the retina of the eye or a screen or image plane of the video camera, which images are in the form of a moiré pattern having a plurality of fringes. When the refraction index of the fluid is changed, the moiré pattern changes as well.

In the above specific example, the two lenses of the enclosure are selected such that the whole enclosure has optical power close to zero when filled with the fluid in the reference state, so that an infinite fringe (i.e. no moiré pattern), which is observed in that state, constitutes the predetermined reference image. When the state of the fluid changes, the refraction index changes as well and a moiré pattern distinguishable by the viewer is obtained. This is the changed image which is easy to be identified visually or by a sensor.

The method of the present invention effectively uses qualitative comparison and identification of optical images instead of quantitative assessment or measurement. The former may be done by naked eye or by sensors through quite simple, cheap and reliable optical systems. Moreover, the identification may be done by a non-qualified observer such as a user of a fluid product, following simple instructions and exemplary patterns.

Contrary to methods of measurement, the designer of the optical arrangement implementing the method of the invention has previous knowledge of the optical parameter both in the reference state and in the changed state of the fluid, so that he can design his system accordingly to make the changed state of the fluid highly distinguishable. Therefore, the arrangement may be adjusted for easy identification of a small change of the optical parameter without measuring it.

The present invention may be used for a wide variety of applications pertinent to detection of changes in the state of liquids, gases, mixtures, suspensions and like, such as production, storage, packaging and monitoring of chemicals, oil, medicines, food, drinks, water, etc.

BRIEF DESCRIPTION OF THE DRAWINGS

In order to understand the invention and to see how it may be carried out in practice, specific embodiments will now be described, by way of non-limiting example only, with reference to the accompanying drawings, in which.

DETAILED DESCRIPTION OF THE INVENTION

Figure 1:
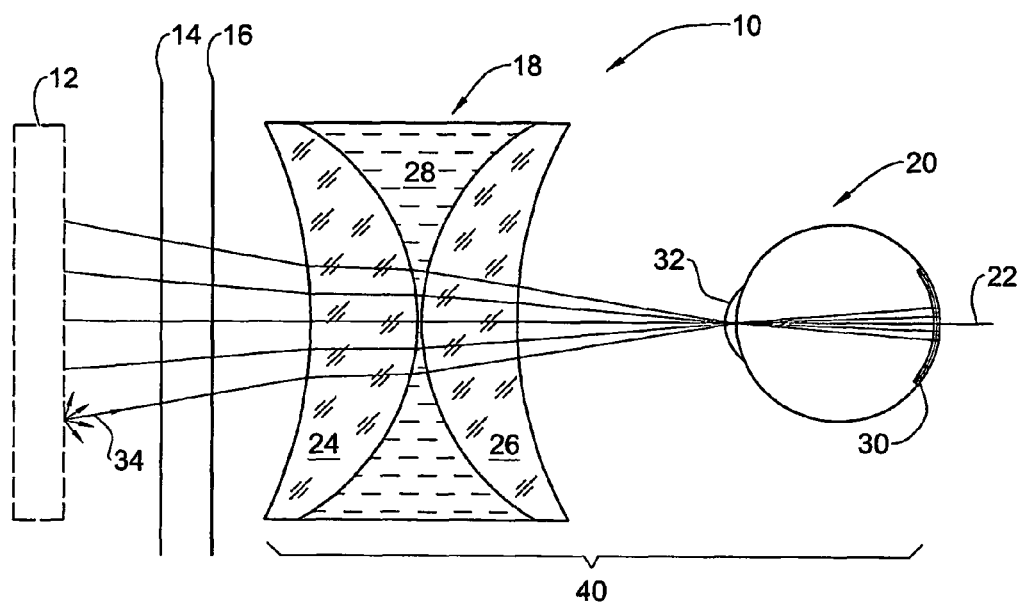
FIG. 1 is a schematic illustration of an optical arrangement for identification of changes in the state of a fluid by naked eye, in accordance with the embodiment of the present invention.

With reference to FIG. 1, there is schematically shown one example of an optical arrangement 10 in accordance with the present invention. The optical arrangement comprises two gratings 14 and 16 that may be illuminated by ambient light or by a light from a diffuse light source 12 which, being optional, is shown in dotted lines. The arrangement 16 further comprises a transparent enclosure (cuvette) 18 with an axis coinciding with the direction of observation 22 via the enclosure 18 of the gratings 14 and 16, by the eye 20 of the observer.

The source 12 may be any common fluorescent or incandescent lamp. The gratings 14, 16 are common Ronchi rulings with identical period. The cuvette 18 is built of two concavo-convex lenses 24, 26, whose convex faces are almost touching. A cavity 28 formed between the lenses is adapted to be filled with a liquid to be monitored. The liquid may be any liquid whose state changes in time. The liquid's original state is considered to be a reference state, and it differs from the changed state in a known manner, i.e. these states have different known indices of refraction. The radii of curvature of the lenses' surfaces are selected so as to minimize distortion of the image while keeping the overall optical power of the cuvette filled with liquid in the reference state close to zero.

The source 12 emits light in all directions and illuminates the gratings 14 and 16 with diffuse light. The eye 20 projects images of the gratings 14, 16 on the retina 30 where a moiré pattern is formed. The pupil 32 filters the rays such that only a small portion 34 reaches the retina 30.

The cuvette 10 and the eye 20 comprise an imaging system 40 focused on the space between the gratings 14, 16. The eye adjusts its focal length such that both gratings are projected on the retina 30 simultaneously.

The size of each of the grating images on the retina is determined by the magnification of the imagining system 40, which depends on the object and image distances. The gratings 14, 16 have different positions along the optical axis 22; hence the respective magnifications are different when the cuvette 18 has non-zero optical power. The projected images thus have different periods which induce a moiré pattern (fringe), whose frequency or orientation depends on the actual magnification difference. The two gratings are rotated slightly relative to one another, and the system magnification defines the moiré fringe orientation. The liquid in its reference state, having reference refraction index, is characterized by a reference moiré pattern with predetermined frequency or orientation.

When the liquid changes its state, thereby changing the refractive index, the optical power of the cuvette 18 changes, together with the magnifications of the two gratings 14, 16. The projected images of the gratings change and produce a changed moiré pattern which has different fringe orientation from the reference moirépattern. As will be shown below, the difference in the fringes is easily identifiable by naked eye.

Calculations

From the laws of geometrical optics, it is easy to derive the following formula:

$$F_S = \frac{P}{d \cdot M \cdot \Delta D}$$

where $F_S$ is the fringe shift in mm, d is the grating gap, P is the grating period, and $\Delta D$ is the optical power difference between optical powers of the lens 18 filled with fluid in reference state and lens 18 filled with the fluid in the changed state. M is the magnification of the optical system 40, which in the FIG. 1 is about 0.6 (the diameter of the projected image divided by that of the input beam, i.e. of the lens). The value of d is 2.4 mm (see below) and P is 0.025.

The optical power of the liquid lens in the cuvette is 2(n−1)/R, where n is the refraction index of the liquid and R is radius of curvature of the internal surfaces of the lenses 24 and 26. Taking R=6 mm and $\Delta n$=0.02 (the refraction index difference between the two states of the liquid), we find:

$\Delta D = 2\Delta n/R = 0.0067 \text{ mm}^{-1}$

Finally, $F_S = 0.025/(2.4 \times 0.6 \times 0.0067) = 2.7 \text{ mm}$

This result may be interpreted as follows. If the cuvette 18 is adjusted to have zero optical power with the liquid in reference state, this will yield infinite fringe in the eye, i.e. no moiré pattern. When the liquid changes its state and the refraction index changes by 0.02, the projected gratings will yield moiré pattern with period 2.7 mm which should be visible.

If the gratings are so oriented that their rulings are tilted relative to each other, the changes in the state of the fluid will cause a change of the orientation of the pattern. For example, when the period of the reference fringes is 0.3 mm, a fringe shift $F_S$=2.7 mm will induce a fringe angle of 0.3/2.7=0.11 rad or 6° deg. This is the approximate angle that may be distinguished by humans comparing visible pattern to a memorized pattern.

In order to have both gratings in focus on the retina, a depth of field is required that encompasses both gratings. To achieve a sufficient depth of field the iris aperture must be as small as possible, which requires strong ambient light in the room. However, the small aperture is subject to the following constraints: a) the transmitted light intensity must be sufficient to obtain good pattern visibility; b) diffraction effects from the aperture should not blur the image.

The sensitivity of the device is proportional to the magnification difference between the two states of the liquid, which in its turn depends on the spatial frequency of the grating and the distance between the two gratings. Good sensitivity requires a large gap, however, the depth of field constraint discussed above limits this parameter. Furthermore, diffraction effects limit the grating gap to a whole multiple of the so-called Talbot distance, determined by the diffraction properties of the gratings. The Talbot distance for the above example is ~1.2 mm and the largest gap that could be achieved before the onset of fringe blurring was 2×1.2=2.4 mm.

Figure 2:
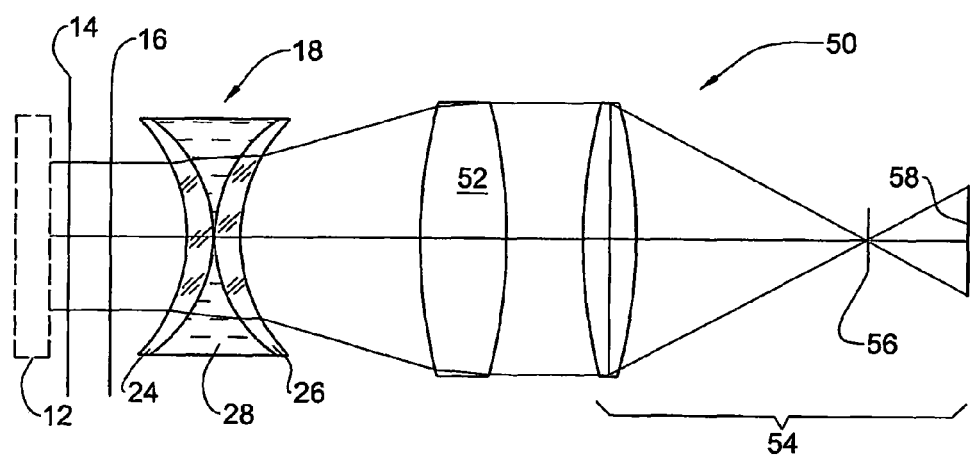
FIG. 2 is a schematic illustration of an optical arrangement for identification of changes in the state of a fluid by projecting visible patterns on a screen, in accordance with another embodiment of the present invention.

With reference to FIG. 2, there is shown an example of the optical arrangement of the present invention. The optical arrangement 50 differs from the one shown in FIG. 1 in that it comprises a collimating biconvex lens 52, a camera with a camera lens 54 and aperture 56, and screen 58. The other elements are similar to those in FIG. 1 and are designated with the same reference numerals.

The principle of operation is the same as that of the arrangement in FIG. 1. However, the images of the gratings 14, 16 are projected on the screen 58 instead of the retina of the eye.

The usage of two lenses with convex faces almost touching, as in the above embodiments, allows identification of turbid or highly absorptive fluids because the fluid layer between convex faces may be made very thin and transparent.

Figure 3:
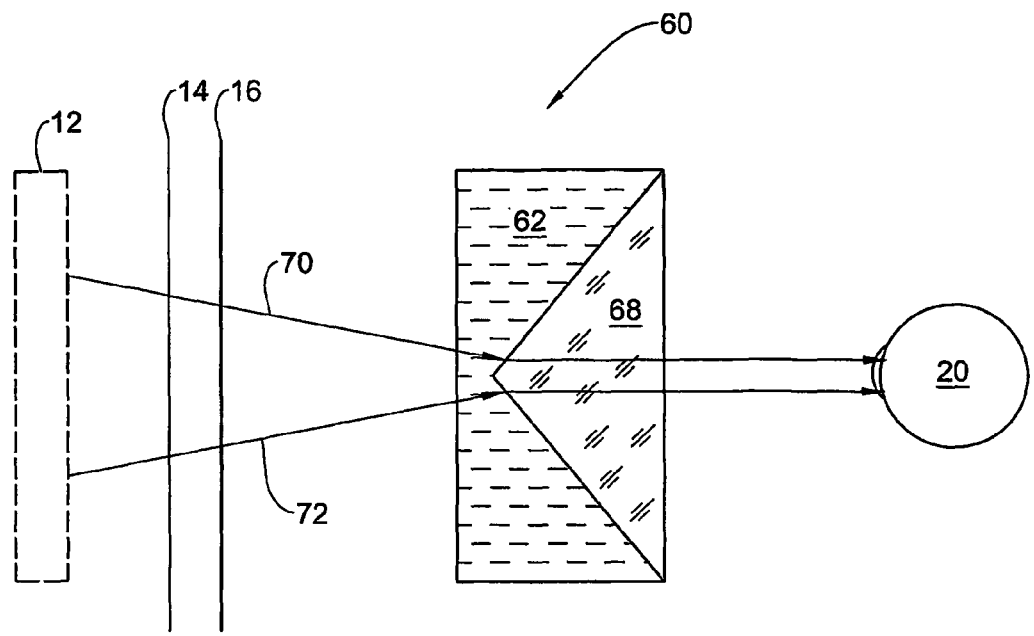
FIG. 3 is a schematic illustration of an optical arrangement for identification of changes in the state of a fluid using a prism, in accordance with still another embodiment of the present invention.

With reference to FIG. 3, a schematic optical arrangement 60 is shown, making use of a transparent prismatic enclosure (double prism) 62. The optical arrangement 60 further includes two gratings 14 and 16. The prismatic enclosure 62 has a compensating prismatic wall 68. The gratings are illuminated by ambient light or by light from a diffuse light source 12, while their images and fringe patterns formed therefrom are observed by the eye 20.

An upper ray 70 of diffused light is deflected upwards at the prism interface. The fringe pattern in the upper half of the enclosure 62 is thus shifted in a direction perpendicular to the fringe direction. The magnitude of the shift is proportional to the deflection angle which depends on refractive index difference across the interface. A lower ray 72 deflects in the opposite direction, inducing a fringe shift in a direction opposite to the shift in the upper half of the enclosure 62. The viewer 20 observes a step (discontinuity) in the fringe pattern between the two halves of the enclosure.

Preferably, the compensation prism 68 is selected such that the step is zero when the fluid in the enclosure 62 is in the reference state, i.e. the fringe pattern will look continuous. With the fluid in changed state, having different refraction index, the viewer will observe an interruption in the middle of the fringe pattern.

Figure 4:
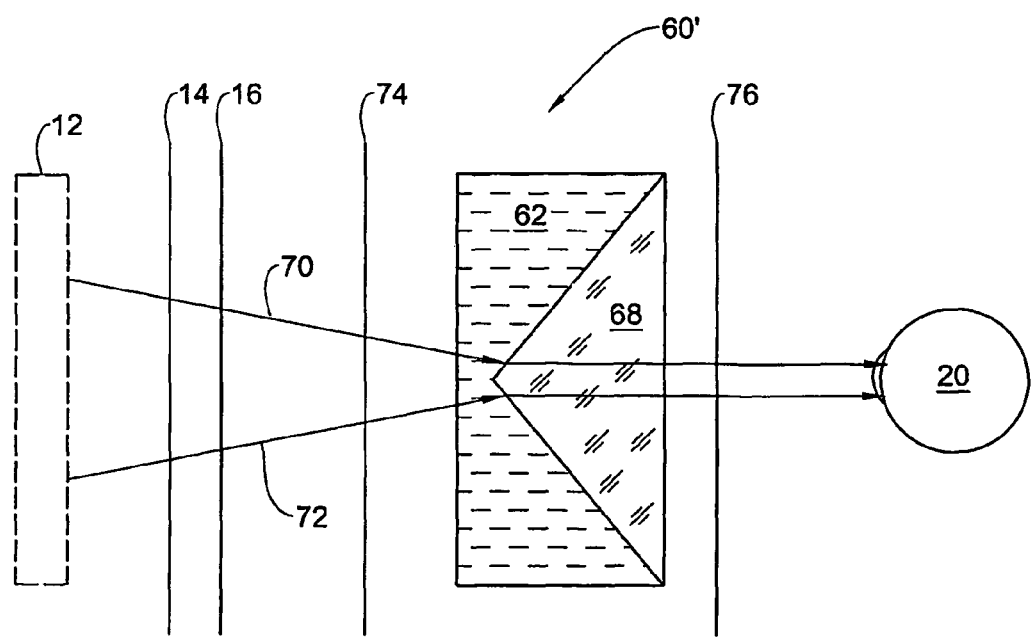
FIG. 4 is a schematic illustration of the optical arrangement of FIG. 3 enhanced by additional polarization filters.

With reference to FIG. 4, a schematic optical arrangement 60' is shown, which is similar to that in FIG. 3 but further includes two polarizing filters 74 and 76. The polarizers 74 and 76 are preferably mounted with perpendicular angles of polarization. They may be used with fluids which, in the changed state, change their angle of polarization, thereby allowing to identify smaller changes of the refraction index.

Figure 5:
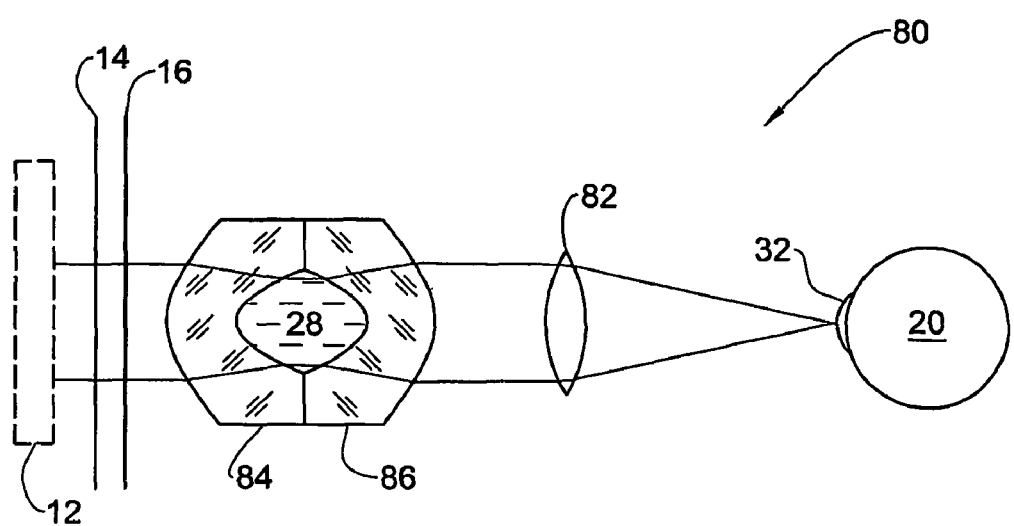
FIG. 5 is a schematic illustration of an optical arrangement for identification of changes in the state of a fluid using aspheric lens enclosure.

With reference to FIG. 5, a schematic optical arrangement 80 is shown, where aspherical lenses 84 and 86 are used to define a transparent enclosure (cuvette) 88. The light source 12 and the gratings 14, 16 are similar to the ones in the arrangements shown in FIGS. 1 to 4. A collimator lens 82 focuses the image of the gratings in the eye 20 or on a screen.

The aspheric surfaces reduce spherical aberration, thus producing straight fringes. This increases the domain of straight fringes over the entire aperture of the optical system. Thereby, differences between fringe orientations in the reference state of the fluid and in the changed state appear more distinctive.

The example shows both inner and outer cuvette surfaces as aspheric but some of them may be just plane.

All embodiments of the inventive system may use ambient light instead of a lamp or other source of diffuse light. Light outside the visible spectrum may be used, such as UV or IR light. In this case, the identification may be performed by suitable sensors in cooperation with logical circuits (microprocessors), or the optical system may be equipped with a converter to visible light allowing visual identification.

The invention claimed is:

1. An optical arrangement for identification of a changed state of a fluid with respect to a reference state of said fluid, the fluid having a refraction index that changes with the change of the state of said fluid, said arrangement comprising
   a) a transparent enclosure adapted to be filled with at least a portion of said fluid;
   b) an object observable through said enclosure;
   c) an optical system having an optical axis and enabling the observation of said object when illuminated by diffuse light, via said enclosure filled with said fluid;
the optical arrangement being designed such that an image of said object observed in the changed state of the fluid is optically distinctive from an image of said object observed in said reference state of the fluid due to a change of the refraction index, at least one of said reference image and said changed image being predetermined, so that said identification can be performed by comparing a current image of said object to the predetermined image, and
wherein a polarization angle of said fluid also changes with the change of the state of the fluid, and said optical arrangement includes two polarization filters, one at each side of said enclosure.

2. The optical arrangement of claim 1, wherein said two polarization filters are rotated at 90° with respect to each other.

* * * * *